(12) United States Patent
Sim et al.

(10) Patent No.: US 9,675,712 B2
(45) Date of Patent: Jun. 13, 2017

(54) PH SENSITIVE FLUORESCENT POLYDIACETYLENE LIPOSOME AND DELIVERY VEHICLE COMPRISING SAME

(71) Applicant: KOREA UNIVERSITY RESEARCH AND BUSINESS FOUNDATION, Seoul (KR)

(72) Inventors: Sang Jun Sim, Seoul (KR); Sang Ho Won, Gangwon-do (KR); Jong Uk Lee, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 17 days.

(21) Appl. No.: 14/418,341

(22) PCT Filed: Jul. 2, 2013

(86) PCT No.: PCT/KR2013/005860
§ 371 (c)(1),
(2) Date: Jan. 29, 2015

(87) PCT Pub. No.: WO2014/007517
PCT Pub. Date: Jan. 9, 2014

(65) Prior Publication Data
US 2015/0182640 A1    Jul. 2, 2015

(30) Foreign Application Priority Data

Jul. 4, 2012 (KR) .................. 10-2012-0072942

(51) Int. Cl.
*A61K 9/127* (2006.01)
*A61K 47/12* (2006.01)
(Continued)

(52) U.S. Cl.
CPC ........ *A61K 49/0084* (2013.01); *A61K 9/1271* (2013.01); *A61K 9/1272* (2013.01);
(Continued)

(58) Field of Classification Search
None
See application file for complete search history.

(56) References Cited

U.S. PATENT DOCUMENTS 4,789,633 A * 12/1988 Huang .................. A61K 9/127
264/4.1
6,730,322 B1    5/2004 Bernstein et al.
(Continued)

FOREIGN PATENT DOCUMENTS

| KR | 1020090078512 A | 7/2009 |
| WO | 2005107712 A1 | 11/2005 |
| WO | 2010091078 A2 | 8/2010 |

OTHER PUBLICATIONS

Guo, Caixin, et al. "A promising drug controlled-release system based on diacetylene/phospholipid polymerized vesicles." Langmuir 25.22 (2009): 13114-13119.*
(Continued)

*Primary Examiner* — Nissa Westerberg
(74) *Attorney, Agent, or Firm* — Hultquist, PLLC; Steven J. Hultquist

(57) ABSTRACT

The present invention relates to a drug delivery vehicle comprising a polydiacetylene liposome, wherein a lipid bilayer is formed by a mixture of 10,12-pentacosadiynoic acid (PCDA), 1,2-dioleoyl-sn-glycero-3-phosphoethanolamine (DOPE), and N-palmitoyl homocysteine (PHC), and a drug to be delivered is encapsulated in an isolated inner space of a polydiacetylene liposome. The PDA liposome drug delivery vehicle of the present invention comprises a lipid layer formed by mixing different phospholipids, excluding polydiacetylene, so as to be stable, and thus
(Continued)

any leakage problems of an encapsulated drug are eliminated. In addition, since the liposome is sensitive to a pH, the shape and size thereof can be readily changed through the formation of a liposome-liposome conjugate by the improved sensitivity of the drug delivery vehicle under a specific acidic requirement, thereby enabling selective drug release, and thus can be applied as a drug delivery vehicle for various target materials. Additionally, the release of a drug can be controlled by controlling a pH requirement of the surroundings, and a drug release process can be monitored in real time through the fluorescence expressed by the stimulation to the surroundings.

8 Claims, 7 Drawing Sheets

(51) Int. Cl.
| | |
|---|---|
| A61K 47/18 | (2017.01) |
| A61K 47/20 | (2006.01) |
| A61K 49/00 | (2006.01) |
| A61K 47/24 | (2006.01) |
| A61K 31/43 | (2006.01) |

(52) U.S. Cl.
CPC ............... *A61K 31/43* (2013.01); *A61K 47/12* (2013.01); *A61K 47/183* (2013.01); *A61K 47/24* (2013.01); *A61K 49/0019* (2013.01)

(56) References Cited

U.S. PATENT DOCUMENTS

| | | |
|---|---|---|
| 2007/0172813 A1 | 7/2007 | Reppy et al. |
| 2008/0131498 A1 | 6/2008 | Hassan et al. |

OTHER PUBLICATIONS

Connor, J., et al., "pH-sensitive liposomes: Acid-induced liposome fusion", "Proc. Natl. Acad. Sci.", Mar. 1984, pp. 1715-1718, vol. 81.
Guo, X., et al., "Mechanism of pH-Triggered Collapse of Phosphatidylethanolamine Liposomes Stabilized by an Ortho Ester Polyethyleneglycol Lipid", "Biophysical Journal", Mar. 2003, pp. 1784-1795, vol. 84, No. 3.

* cited by examiner

PH SENSITIVE FLUORESCENT POLYDIACETYLENE LIPOSOME AND DELIVERY VEHICLE COMPRISING SAME

CROSS-REFERENCE TO RELATED APPLICATIONS

This application is a U.S. national phase under the provisions of 35 U.S.C. §371 of International Patent Application No. PCT/KR13/05860 filed Jul. 2, 2013, which in turn claims priority of Korean Patent Application No. 10-2012-0072942 filed Jul. 4, 2012. The disclosures of such international patent application and Korean priority patent application are hereby incorporated herein by reference in their respective entireties, for all purposes.

TECHNICAL FIELD

The present invention relates to a drug delivery vehicle based on a polydiacetylene liposome, and more particularly, to a novel pH sensitive polydiacetylene liposome prepared by using polydiacetylene and various phospholipids, and a drug delivery vehicle capable of measuring fluorescent intensity by using a property in which the polydiacetylene liposome self-expresses fluorescence by stimulation from surrounding environment, without adding separate fluorescent materials, and capable of monitoring a drug release through fluorescence.

BACKGROUND ART

A liposome is being extensively researched as a drug delivery vehicle due to effective chemical and physical properties in various treatment applications such as drug delivery and biomedical diagnostics. An important factor in the drug delivery vehicle is to accurately release the drug to a target position at which the drug is needed, and to perform a real-time monitoring of the series of processes.

However, the real-time monitoring and the controlling of the drug release are significantly difficult to be performed. In general, a normal liposome has several problems in drug delivery, for example, morphological instability, hydrolysis, oxidation and drug leakage, and the like under a physiological condition. As described above, the existing liposome drug delivery system has a lot of problems to be solved.

In order to overcome the instability and release problem, various types of polymer liposome are being developed, and relative technologies using the existing liposome as a drug delivery vehicle have been disclosed in Korean Patent Publication Nos. 10-0963831, PCT/US 2005/015349, and the like. However, development of a novel liposome capable of real-time monitoring a drug release process and controlling the drug release has acutely demanded.

DISCLOSURE OF INVENTION

The present invention aims to solve instability of the drug delivery vehicle, a release problem, difficulty in real-time monitoring of drug release, and the like, in the liposome drug delivery system, and an object of the present invention is to provide a novel polydiacetylene liposome prepared by polymerization of diacetylene, which is capable of increasing stability to prevent drug leakage, selectively releasing a drug only under a specific environmental condition, and real-time monitoring a drug release process through fluorescence, unlike the existing liposomes, and a drug delivery vehicle including the same.

In order to achieve the foregoing objects, the present invention provides a polydiacetylene liposome having an inner space isolated from a medium by a lipid layer membrane, wherein the lipid layer includes 10,12-pentacosadiynoic acid (PCDA), 1,2-dioleoyl-sn-glycero-3-phosphoethanolamine (DOPE), and N-palmitoyl homocysteine (PHC).

According to an embodiment of the present invention, a mixing molar ratio of the PCDA, DOPE and PHC may be 6:3:1.

According to an embodiment of the present invention, the polydiacetylene liposome sensitively reacts as a pH value of the medium becomes decreased, and therefore, a diameter of the liposome may be increased.

According to an embodiment of the present invention, the polydiacetylene liposome may self-express unique fluorescence by stimulation from an external environment, and may perform real-time monitoring of the fluorescence, and the stimulation from the external environment may be reflected by a change in pH values.

In addition, in order to achieve the foregoing objects, the present invention provides a drug delivery vehicle including a polydiacetylene liposome having an inner space isolated from a medium by a lipid layer membrane, wherein the lipid layer includes 10,12-pentacosadiynoic acid (PCDA), 1,2-dioleoyl-sn-glycero-3-phosphoethanolamine (DOPE), and N-palmitoyl homocysteine (PHC), and a drug to be delivered is encapsulated in the isolated inner space of the polydiacetylene liposome.

According to an embodiment of the present invention, a mixing molar ratio of the PCDA, DOPE and PHC may be 6:3:1.

According to an embodiment of the present invention, as a pH value condition of the medium becomes decreased, a diameter of the polydiacetylene liposome may be increased, and the polydiacetylene liposome may be fused with an adjacent polydiacetylene liposome as a lateral phase of the lipid layer is separated.

According to an embodiment of the present invention, when the polydiacetylene liposome is fused with the adjacent polydiacetylene liposome, the drug in the liposome may be released, and during the drug release, the polydiacetylene liposome may express unique fluorescence.

According to an embodiment of the present invention, the drug may be an anti-biotic drug or an anti-cancer drug.

According to an embodiment of the present invention, the drug delivery vehicle may control a drug release time and a drug release amount, the drug release time and the drug release amount being controlled by the following steps.

According to an embodiment of the present invention, the drug delivery vehicle may control a drug release time and a drug release amount, the drug release time and the drug release amount being controlled by the following steps, and may perform real-time monitoring of the drug release by self-expressing unique fluorescence at the same time:

controlling the drug release time by controlling a pH condition of the medium to be pH 3 to 7 with respect to the drug delivery vehicle;

self-expressing unique fluorescence of the liposome according to a change in a pH condition which is an external stimulation while simultaneously performing the drug release by controlling the drug release time; and confirming and monitoring the drug release and the drug release amount through the fluorescence of the liposome.

Advantageous Effects

A PDA liposome drug delivery vehicle according to the present invention includes a lipid layer formed by mixing different phospholipids with each other so that a drug is stably encapsulated, in addition to polydiacetylene, and therefore, there is no problem in drug leakage. In addition, under an acidic condition, a drug delivery vehicle sensitive to pH may form a liposome-liposome fusion as a pH value is decreased, such that a shape and a size thereof are capable of being easily changed, which allows selective drug release, and may use various target materials depending on a surface due to a COOH group on the surface of the polydiacetylene, such that the drug delivery vehicle may be utilized as an effective drug delivery vehicle. Further, according to the surrounding environment, a drug release time may be controlled, and confirmation and monitoring of the drug release may be performed by fluorescence of the polydiacetylene liposome expressed by stimulation from the surrounding environment, and a drug release amount and a drug release efficiency may be controlled.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Hereinafter, the present invention will be described in detail.

Figure 1A:
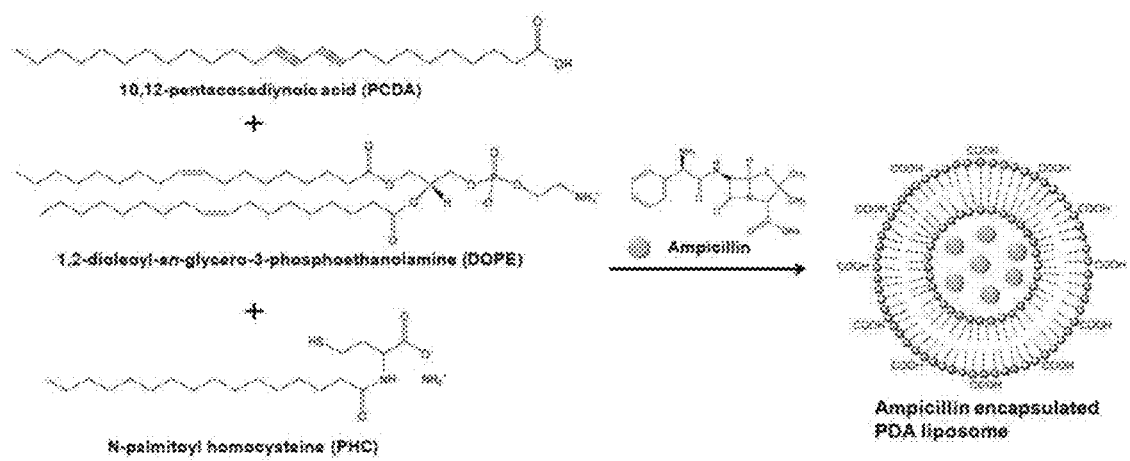
FIG. 1A is a conceptual diagram showing synthesis of a pH sensitive PDA liposome having encapsulated and loaded antibiotic drug ampicillin according to an embodiment of the present invention, and a shape thereof.

The present invention relates to a novel polydiacetylene liposome usable as a drug delivery vehicle. As shown in FIG. 1a below, the polydiacetylene liposome includes a lipid layer formed by mixing lipid monomers of 10,12-pentacosadiynoic acid (PCDA), 1,2-dioleoyl-sn-glycero-3-phosphoethanolamine (DOPE), and N-palmitoyl homocysteine (PHC) with each other, and a drug is stably encapsulated in the lipid layer.

In addition, the present invention relates to a drug delivery vehicle including the polydiacetylene liposome, wherein the drug delivery vehicle has an inner space isolated from a medium by a lipid bilayer membrane, and a drug to be delivered is encapsulated in the isolated inner space.

The lipid monomers consisting of the lipid layer are formed by mixing PCDA, DOPE and PHC with each other, and a mixing molar ratio thereof is 6:3:1.

Figure 1B:
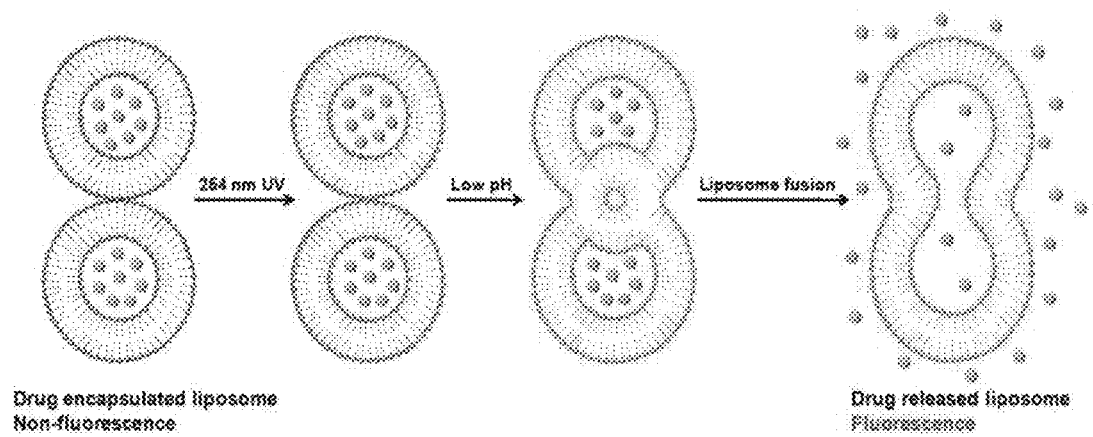
FIG. 1B is a conceptual diagram showing control of ampicillin release under acidic pH condition and monitoring of drug release by fluorescence according to an embodiment of the present invention.

As shown in FIG. 1b below, the PDA liposome according to the present invention has more improved stability as compared to the existing liposomes since a polymer is formed by polymerization of a triple bond of an adjacent diacetylene monomer at the time of UV irradiation, and the PDA liposome may sensitively react under a low pH condition, and may self-express unique fluorescence from external stimulation, and the liposome and an adjacent liposome are fused with each other to increase a size of the liposome, and the drug in the liposome may be released.

In addition, the drug delivery vehicle including the polydiacetylene liposome according to the present invention may control the drug release time, the drug release amount, and the drug release efficiency, and may monitor in real-time the drug release by unique fluorescence of the polydiacetylene liposome expressed from external stimulation.

Specifically, first, since the polydiacetylene liposome according to the present invention is sensitive to the pH, the drug release may be controlled according to a pH condition of the surrounding environment. Further, in addition to the drug release, intensity of the unique fluorescence generated by the drug release may be measured and monitored, and after confirming the drug release amount by the measured fluorescent intensity, the drug release amount and the release efficiency may be controlled by controlling the pH condition of the drug delivery vehicle at a range of pH 3 to 7 again.

As described above, the present invention has various benefits by using the polydiacetylene (PDA) liposome as the drug delivery vehicle. First, polydiacetylene is generally a non-toxic material, and at the time of UV irradiation, the liposome and the adjacent liposome are polymerized by a 1,4-addition reaction to form an ene-yne alternate conjugate backbone polymer chain, thereby forming a cross-linked polymer polydiacetylene liposome, which has much better stability as compared to a non-polymerized liposome. In addition, due to a carboxylic acid in a head part, various ligands and a receptor may be bonded on a surface of the liposome for selective targeting. Further, a degree of polymerization and a drug release rate may be controlled by changing a lipid composition of the liposome. Lastly, the polyacetylene liposome is fused with the adjacent liposome by various pH conditions and external stimulation, the drug encapsulated therein may be released and at this moment, the polydiacetylene liposome is changed from non-fluorescence to fluorescence to effectively perform monitoring of the drug release.

The drug which is capable of being effectively delivered to a target material according to the present invention may include various anti-biotic drugs, anti-cancer drugs, and the like. Hereinafter, experiments using ampicillin will be specifically described in the following Examples.

The ampicillin, a potent antibiotic material having a short-term stability in an aqueous solution, is clinically used for treatment for a wide range of bacterial infections. The ampicillin is encapsulated by using the pH sensitive PDA liposome according to the present invention, and a treatment effect thereof was tested by a plaque analysis method. The plaque analysis aims to grow the isolated plaque of the antibiotic material in a bacterial habitat. A removal of the bacteria growth may be confirmed using an agar medium, and an effect of the antibiotic material on the bacteria may be confirmed. In the pH sensitive PDA liposome in which antibiotic drug ampicillin is encapsulated and loaded, it may be confirmed from the following Examples that the bacteria is remarkably killed even by a low pH condition as described above. In addition, due to a unique change in fluorescence of the PDA liposome, monitoring of the drug release may be easily performed by confirming fluorescent images of the PDA liposome according to a fluorescent microscope analysis.

Specifically, when pH of the medium is decreased from pH 7 to pH 4, the PDA liposomes according to the present invention are rapidly fused with each other, and as the pH is decreased, a size of the PDA liposome is increased approximately by 20 times from 110.0±19.3 nm to 2046.7±487.4 nm.

Accordingly, under a neutral condition, drug leakage is stably prevented by crosslinkage of the diacetylene lipid, and the encapsulated drug is momentarily released under an acidic pH condition. The ampicillin was almost completely released from the liposome within 4 hours under the acidic pH condition (74.4±3.9%), and then a release amount of the ampicillin was analyzed by HPLC. Lastly, a treatment effect was observed by appearance of the plaque in the habitat of *E. coli*, and fluorescent images of the PDA liposome were obtained from the plaque for monitoring of the drug release. As a result thereof, it could be confirmed that the novel pH sensitive polymer liposome according to the present invention is significantly useful as a drug carrier.

Accordingly, under the neutral condition, the drug leakage is stably prevented in the polydiacetylene liposome produced by the triple bond cross-linkage of the diacetylene monomer, and then the encapsulated drug is momentarily released under the acidic pH condition. The ampicillin was almost completely released from the liposome within 4 hours under the acidic pH condition (74.4±3.9%), and then a release amount of the ampicillin was analyzed by HPLC. Lastly, a treatment effect was observed by growing bacteria on a medium, dropping the drug delivery vehicle containing the drug under a pH 4, and confirming appearance of the plaque in the medium, and fluorescent images of the PDA liposome were obtained from the plaque for monitoring the drug release. As a result thereof, it could be confirmed that the novel pH sensitive polymer liposome according to the present invention is significantly useful as a drug delivery vehicle.

Hereinafter, preferable embodiments of the present invention will be described in more detail. These embodiments of the present invention have been described for illustrative purposes, and therefore, the present invention is not limited thereto, and it will be apparent to those skilled in the art that modifications and variations could be made without departing from the scope and the spirit of the present invention as defined by the appended claims.

EXAMPLE

Hereinafter, materials used in the Examples of the present invention are as follows.

10,12-pentacosadiynoic acid (PCDA), 1,2-dimyristoyl-sn-glycero-3-phosphocholine (DMPC), an ampicillin sodium salt, a hydrochloric acid solution, and 0.1 M phosphate buffered saline pH 7.4 (PBS buffer) were purchased from Sigma-Aldrich (Korea).

1,2-dioleoyl-sn-glycero-3-phosphoethanolamine (DOPE) and N-palmitoyl homocysteine (ammonium salt)(PHC) were purchased from Avanti Polar Lipids, Inc. (Alabaster, USA).

LB broth was purchased from Becton, Dickinson and Company (Korea), a plant agar was purchased from Duchefa Biochemie (Haarlem, Netherlands), *E. coli* 0-157(ATCC 43894) was used, and a deionized water (DI, water has a resistance of 18.2 mΩcm$^{-1}$) obtained from water purification system (Human Corporation, Korea) was used to prepare a medium and a buffer.

SYNTHETIC EXAMPLE 1

Synthesis of pH Sensitive PDA Liposome Drug Delivery Vehicle According to the Present Invention Chloroform solutions of PCDA, DMPC, DOPE and PHC were prepared in light brown glass vials at −4° C., respectively. Solutions of PCDA, DOPE and PHC lipid monomers were mixed at a molar ratio of 6:3:1 (PCDA:DOPE:PHC) so as to have a total lipid concentration of 1.0 mM. Then, chloroform was removed by using N2 gas, and a dried layer having residual mixed diacetylene was heated while gently stirring in a circulating water bath set up at 80° C. for 15 mins, and re-suspended in 1.0 mL of 10 mM PBS buffer (pH 7.4), then the prepared solution was repeatedly extruded 10 times by a prefilter-100 nm membrane-prefilter composite. An extruding system was maintained to be 85° C. in order to form PCDA, DOPE and PHC lipids in a dry bath. The extruded solution contained approximately 100 nm of liposome. Then, the liposome solution was dried at room temperature (25° C.) for 20 mins, and stored at 4° C.

COMPARATIVE EXAMPLE 1

Synthesis of the Existing PDA Liposome Drug Delivery Vehicle

Chloroform solutions of PCDA and DMPC were prepared in light brown glass vials at −4° C., respectively. The same method was performed as Synthetic Example 1 above except that the PCDA, and DMPC lipid monomer solutions were mixed at a molar ratio of 8:2 (PCDA:DMPC) so as to have a final concentration of 1.0 mM.

EXPERIMENTAL EXAMPLE 1

Measurement of Size and Zeta Potential of PDA Liposome (1) Size and zeta potential of the PDA liposomes synthesized in Synthetic Example 1 and Comparative Example 1 above were measured by using an electrophoretic light scattering spectrophotometer (ELS-Z, Otsuka Electronics, Tokyo, Japan). Since the polymer liposome has a maximum absorption wavelength of 650 nm, which interrupts the measurement of the particle size, after the liposome solution was prepared for the measurement of the particle size, UV light irradiation was not performed on the prepared liposome solution.

(2) Size and stability of PDA liposome

Zeta potential (a degree of repulsion between liposomes) and size of the PDA liposomes synthesized in Synthetic Example 1 (PCDA/DOPE/PHC) and Comparative Example 1 (PCDA/PDA) above were measured by using an electrophoretic light scattering method, and results thereof were shown in the following Table 1.

TABLE 1

|  | Comparative Example 1 | Synthetic Example 1 |
|---|---|---|
| Composition | PCDA:DMPC (8:2) | PCDA:DOPE:PHC (6:3:1) |
| Average diameter (nm) | 135.0 ± 54.8 | 111.6 ± 23.5 |
| pH 4 Average diameter (nm) | 258.6 ± 72.2 | 995.5 ± 240.3 |
| Rate of increase (%) | 91.5 | 792 |
| Zeta potential (mV) | −12.54 ± 1.29 | −7.15 ± 0.43 |
| polydiversity | 0.27 ± 0.03 | 0.23 ± 0.03 |

Stability of a colloidal system may be predicted and controlled by the zeta potential which is a significant indicator of charges on the colloidal surface. In Table 1, the zeta potential values of these two types of liposome had negative values (−7.15 to −12.54 mV), since charged lipids such as PCDA (negative) and PHC (negative) were positioned in the liposomes. The PCDA has a carboxylic acid group in a head part. The carboxylic acid group is weakly ionized in an aqueous solution to increase the negative charges on the surface of the liposome. The liposome into which the charged lipids are inserted exhibits an excellent assembly when it is determined that the zeta potential value is high. The liposome consisting of PCDA, DOPE and PHC (a molar ratio is 6:3:1) of Synthesis Example 1 (hereinafter, referred to as a PCDA, DOPE and PHC liposome) has a zeta potential value (−7.15 mV) which is lower than the zeta potential (−12.54 mV) of the liposome consisting of PCDA and DMPC (a molar ratio is 8:2) of Comparative Example 1 (hereinafter, referred to as a PCDA and DMPC liposome), since a molar ratio of the DOPE or the DMPC having neutral charges, that is, zwitter ions is increased. In addition, a fraction of the PCDA was decreased. Due to these values, aggregation of the PDA liposome may be decreased by electrostatic repulsion force and stability may be maintained.

Under neutral pH, both of the liposomes of Synthetic Example 1 and Comparative Example 1 had sizes which are similar to each other at a range of 100-150 nm. Each size of the liposomes was measured again under an acidic pH condition (pH 4), and compared with the sizes before the acid treatment to confirm an effect of pH on the PDA liposome. After the acid treatment, the PCDA and DMPC liposome of Comparative Example 1 showed a small increase in sizes as compared to the case before the acid treatment. Meanwhile, after the acid treatment, the PCDA, DOPE and PHC liposome of Synthetic Example 1 had an increased size approximately 10 times. Therefore, it may be appreciated that since the PCDA, DOPE and PHC liposome of Synthetic Example 1 according to the present invention is significantly sensitive to acidic pH, which is significantly useful as the drug delivery vehicle.

EXPERIMENTAL EXAMPLE 2

Characteristic Analysis of Properties of pH Sensitive PDA Liposome by Change in pH Values (1) 0.5 to 2 L of HCl in various concentrations were added to the liposome solution, and strongly mixed with each other to maintain a predetermined pH, and shapes and sizes of the liposomes were analyzed by characteristics by using a high-resolution transmission electron microscope (HR-TEM, Tecnai 20, operated under an acceleration voltage of 200 kV) and electrophoretic light scattering spectrophotometer (ELS-Z).

The liposome solution was attached onto a carbon-coated copper grid. After drying, the sample was analyzed by HR-TEM. An average particle size distribution of the PDA liposome was measured under various pH conditions by ELS-Z, and each experiment was repeated three times, and each result was determined as an average value of values measured by the three repeated experiments. In these experiments, all liposomes were blank liposomes into which the drug was not trapped.

(2) Effect of pH values on pH sensitive PDA liposome

The shapes and sizes of the pH sensitive liposome in which the drug was not loaded were analyzed by characteristics under different pH values by HR-TEM and electrophoretic light scattering method, and results thereof were shown in FIGS. 2 and 3 below. In addition, a change in the shape of the PDA liposome induced by the acid was analyzed by HR-TEM.

Figure 2A:
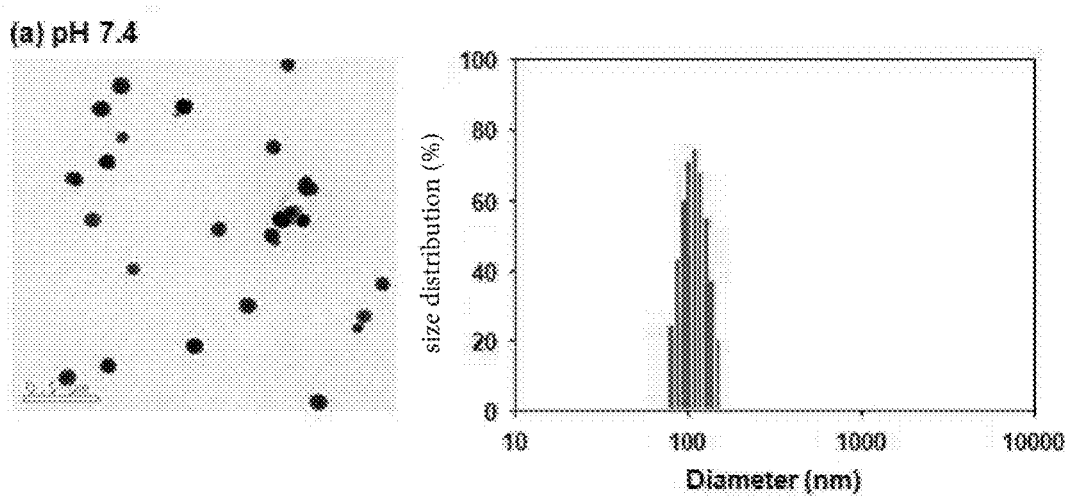
FIGS. 2A, 2B, and 2C show TEM images and size distribution diagram of the PDA liposome according to the present invention under various pH conditions, wherein the liposome has an average diameter of 110 nm at (a) pH 7.4, 355 nm at (b) pH 6.5, and 2047 nm at (C) pH 3.3, respectively.
Figure 2B:
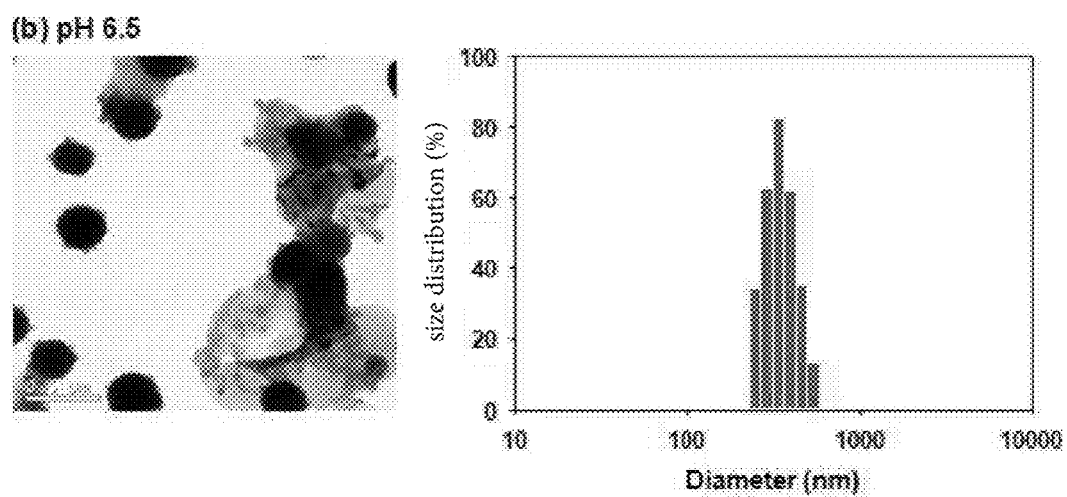
Figure 2C:
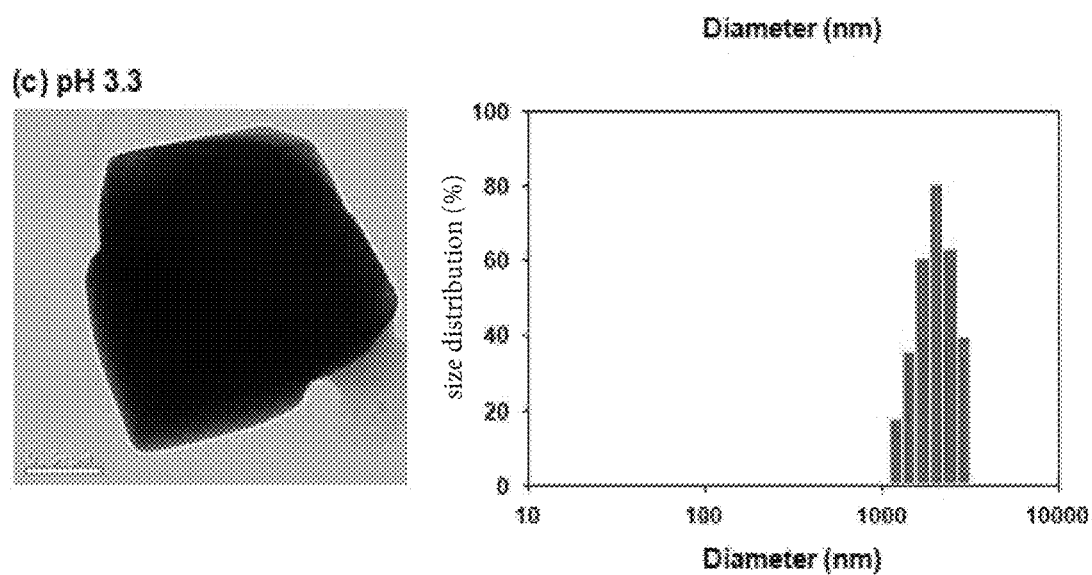

FIG. 2a below is a typical image of the PDA liposome consisting of PCDA, DOPE and PHC (a molar ratio is 6:3:1) of Synthetic Example 1. 6:3:1 The PCDA, DOPE and PHC (a molar ratio is 6:3:1) polymer PDA liposome has a spherical structure, and an average diameter of 110.0±19.3 nm at pH 7.4. After 0.8 µl of HCl was added to 2 mL of the liposome solution (pH 6.5), the liposome was increased to have a diameter of 354.5±73.9 nm. FIG. 2b shows that the liposomes are partially aggregated and fused with each other. However, the most of the liposomes maintained a vesicle structure thereof, since the polymer liposome has resistance to the change in the shape induced by the acid. Lastly, when 1.7 µl of HCl was added to 2 mL of the liposome vesicle (pH 3.3), the liposome was much larger. As a result, as shown in FIG. 2c, most of the liposomes were fused with each other and had an average diameter of 2046.7±487.4 nm.

Figure 3:
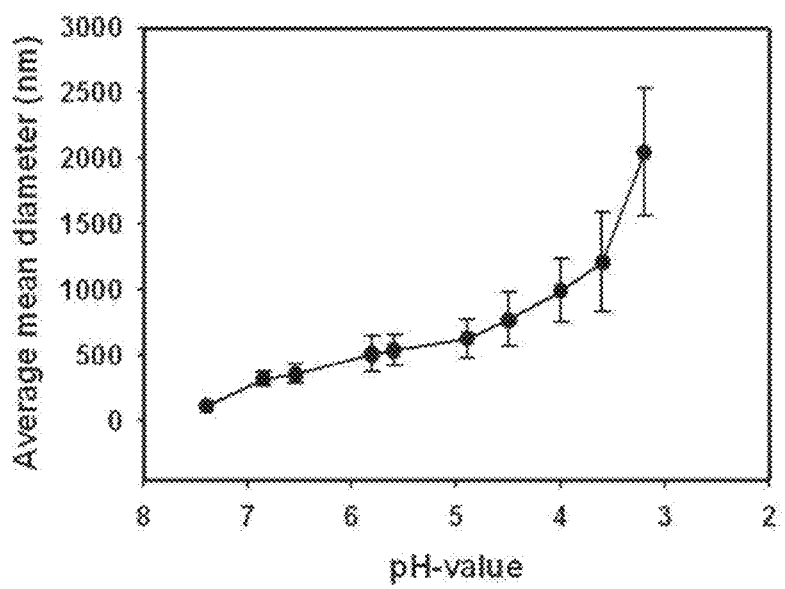
FIG. 3 is a graph showing an average diameter of each PDA liposome prepared by adding acids in various volumes to the PDA liposomes according to the present invention, under various pH conditions.

FIG. 3 below shows a particle size distribution curve of the PDA liposomes under various pH conditions. After the acid treatment, the average diameter of the liposome was increased approximately 20 times from 110.0±19.3 nm to 2046.7±487.4 nm, which suggests that when the pH is low, the liposome becomes larger. Two main reasons in these results are as follows. First, a bilayer solubility of the protonated PHC is low to form domains of the PHC under an acidic pH condition. The separation of the lateral phase of the lipid bilayer may be a main reason of the fusion. Second, the presence of the DOPE promotes liposome fusion induced by the acid. The DOPE tends to form a hexagonal phase or a reversed micelle.

SYNTHETIC EXAMPLE 2

Synthesis of pH Sensitive Liposome (Synthesis Example 1) Having a Loaded Drug

Chloroform solutions of PCDA, DMPC, DOPE and PHC were prepared in light brown glass vials at −4° C., respectively. Solutions of PCDA, DOPE and PHC lipid monomers were mixed at a molar ratio of 6:3:1 (PCDA:DOPE:PHC) so as to have a total lipid concentration of 1.0 mM. Then, chloroform was removed by using N2 gas, and a dried layer having residual mixed diacetylene was heated while gently stirring in a circulating water bath set up at 80° C. for 15 mins, and re-suspended in ampicillin (0.02 mg/mL) in 1.0 mL of PBS buffer (pH7.4). Then, the prepared solution was repeatedly extruded 10 times by a prefilter-100 nm membrane-prefilter composite. An extruding system was maintained to be 85° C. in order to form PCDA, DOPE and PHC lipids in a dry bath. The extruded solution contained approximately 100 nm liposome having loaded ampicillin.

Next, the liposome solution was cooled to room temperature (25° C.) for 20 mins. The solution was transferred on a Petri dish on ice, and irradiated at 254 nm UV for 15 mins in order to cross-link the polymer liposome. The ampicillin remaining in the liposome having the loaded drug and the solution in a free state, was removed by using a size exclusion column (Sephadex G25).

COMPARATIVE EXAMPLE 2

Synthesis of the Existing Liposome (Comparative Example 1) in which a Loaded Drug Chloroform solutions of PCDA and DMPC were prepared in light brown glass vials at −4° C., respectively. The same method was performed as Synthetic Example 2 above except that the PCDA and DMPC lipid monomer solutions were mixed at a molar ratio of 8:2 (PCDA:DMPC) so as to have a final concentration of 1.0 mM.

EXPERIMENTAL EXAMPLE 3

Preparation of Medium for Bacterial Growth

In order to prepare an LB broth and an agar medium, 12.5 g of the LB broth and 7.5 g of the plant agar were transferred to 1 L sterile flask. The components were dissolved in 500 mL of distilled water or deionized water, and flask was tightly covered with an aluminum foil, a plug or a cap similar thereto. The mixture was heated until a boiling point was reached to dissolve the agar, and sterilized by autoclave at 121-124° C. for 15 mins, and then waited until the autoclave was cooled and a pressure was 0. The medium was removed from the autoclave and cooled to room temperature. When the LB agar was cooled to a temperature (approximately 45° C.) which is still considered hot by touch, 0.5 cm or ¼ layer of agar was poured into the Petri dish. It corresponds to approximately 20 to 25 mL volumes of the agar. The Petri dish was positioned on a flat surface until the agar was completely solidified for 30 to 40 mins. The Petri dish containing the solid agar was stored at 4° C.

EXPERIMENTAL EXAMPLE 4

Culture and Growth of Bacteria

300 µl of bacteria (*E. coli*) was added to 3.0 mL of the LB broth, and the culture fluid was strongly shaken. Then, the culture fluid was cultured in an incubator shaking the bacteria at 37° C. overnight. After a temperature of the solid agar plate was pre-heated in an incubator at 37° C. to decrease the aggregation, 200 µl of the bacterial culture fluid was rapidly poured onto the agar surface of the mild plate. The *E. coli* culture fluid was smeared onto the agar plate containing the medium to absorb the *E. coli* onto the agar medium for 15 mins.

EXPERIMENTAL EXAMPLE 5

Anti-Bacterial Analysis of Drug Release In Vitro

Six Petri dishes containing the solid agar and the fusional bacteria were prepared. First, a PBS buffer (pH 4.0), a drug-encapsulated liposome solution, an acid-treated drug-encapsulated liposome solution (pH 4), an ultrasonic-treated drug-encapsulated liposome solution, and an ampicillin standard solution were diluted to have a concentration of 0.02 M. Then, 20 µl of each solution was dropped in the center of each Petri dish. Then, the Petri dish of which the lid was covered was reversed so as to prevent moisture from being transferred on the LB agar, and the reversed plate was left in an incubator at 37° C. overnight.

The control groups (the non-treated liposome, plate culture using the PBS buffer (pH 4), and plate culture using the suspended drug-encapsulated liposome in the PBS buffer) were used under the same condition, and after 8 to 12 hours, the plaque which is a removal region could be observed in the bacterial habitat on the plate.

EXPERIMENTAL EXAMPLE 6

Quantitative Analysis of Ampicillin by HPLC

Characteristic-analysis of ampicillin release was conducted by high performance liquid chromatography (HPLC) at room temperature from Comparative Example 2 in which a molar ratio of PCDA/DMPC is 8:2, and Synthetic Example 2 in which a molar ratio of PCDA/DOPE/PHC is 6:3:1. Quantitative analysis of the ampicillin was performed by using Agilent HPLC system (Agilent Technologies, U.S.A.) provided with a reversed phase C-18 column (Xbridge, RP-18, 250×4.6 mm, 5 um, Waters Co.), pump (Agilent Technologies 1200 series), an automatic injector (Agilent Technologies, 1200 series), and UV/visible light detector (Agilent Technologies, 1100 series). A mobile phase was 0.575% ammonium acetate of methanol:water (450:550, v/v) controlled to be pH 7.2. A range of the ampicillin standard solution was 5-100 µg/mL, and a black curve was a straight line type, and $r^2$ values were present within a range of 0.93 to 1.0. Injection volume of the ampicillin standard solution and the sample was 1 mL, and a column was operated under a pressure of 100 bar, and a flow velocity of the mobile phase was 0.6 mL/min, and absorbance was detected at a wavelength of 230 nm. Three samples were taken from each injected material and an area below a peak was measured each time. Analysis of each experimental system was performed on the standard material and the control groups at the same date.

In order to measure a total amount of the ampicillin loaded in the liposome, the polymer liposome was dissolved with ethanol having an increased volume by 10 times. 0.2 mL of the ampicillin-encapsulated liposome solution was dissolved in 2 mL of ethanol. Then, the liposome swelling solution was mixed for 5 mins, and filtrated through 0.22 μm of a disposable filter. 0.8 μl of HCl was added to 1 mL of the ampicillin-encapsulated liposome solution, and in order to measure a release amount of the ampicillin from the liposome under the acidic pH condition, the mixture was prepared to be pH 4. The releasing process continued for 12 hours. Two values, that is, the total amount of the ampicillin loaded in the liposome, and the release amount of the ampicillin from the liposome were analyzed by HPLC without additional treatment.

EXPERIMENTAL EXAMPLE 7

Fluorescent Analysis for Monitoring of Drug Release

In order to confirm a possibility of the monitoring of the drug release, and difference between Comparative Example 2 and the novel pH sensitive liposome of Synthetic Example 2 according to the present invention, fluorescent image and fluorescent intensity of each PDA liposome were analyzed by fluorescent microscope analysis.

The fluorescent microscope was composed of four main units as follows. A microscope, a fluorescent unit (a mercury arc lamp as a light source, which was composed of Nikon G2A filter suitable for analysis of a fluorescent device and a red color PDA fluorescence), a digital camera unit (Infinity, U.S.A.), and photo analysis software (i-solution, Korea).

The fluorescent signals derived from the PDA liposome spots were visualized in the system, and digital microscope images were obtained. Intensity of the spots was calculated by the photo analysis software. Intensity was indicated as an average intensity value of each pixel, and had a value of 0 to 255 by the digital photo analysis, wherein 0 is the minimum value and 255 is the maximum value.

(1) Quantitative Analysis of Ampicillin Encapsulation

The novel pH sensitive PDA liposome consisting of PCDA, DOPE and PHC according to the present invention has a property of controlling the drug release under an acidic pH condition, and the property thereof was confirmed in comparison with the existing PDA liposome consisting of PCDA and DMPC.

The following Table 2 shows encapsulation efficiency and drug content between the existing PDA liposome consisting of PCDA and DMPC and the novel pH sensitive PDA liposome consisting of PCDA, DOPE and PHC according to the present invention.

TABLE 2

| | Composition | Encapsulation efficiency (%) | Drug content |
|---|---|---|---|
| Comparative Example 2 | PCDA:DMPC (8:2) | 62.89 ± 0.87 | 11.67 ± 0.01 |
| Synthetic Example 2 | PCDA:DOPE:PHC (6:3:1) | 60.41 ± 1.82 | 10.83 ± 0.03 |

The encapsulation efficiency (%) and the drug content (%) were calculated by the following Equations, respectively.

Encapsulation efficiency (%)=(an actual amount of the ampicillin encapsulated in the liposome/an injection amount of the ampicillin in the liposome dispersion)×100

Drug content (%)=(an actual amount of the ampicillin encapsulated in the liposome/a total amount of lyophilized liposome)×100

As shown in Table 2 above, the encapsulation efficiency and the drug content between the PCDA/DMPC liposome and the PCDA/DOPE/PHC liposome were measured as 62.89±0.87%, 11.67±0.01% and 60.41±1.82%, 10.83±0.03%, respectively. That is, these liposomes were not significantly different in view of the encapsulation efficiency and the drug content. Therefore, a lipid type and a lipid composition of the liposome do not have a remarkable effect on load volume of the drug.

Figure 4:
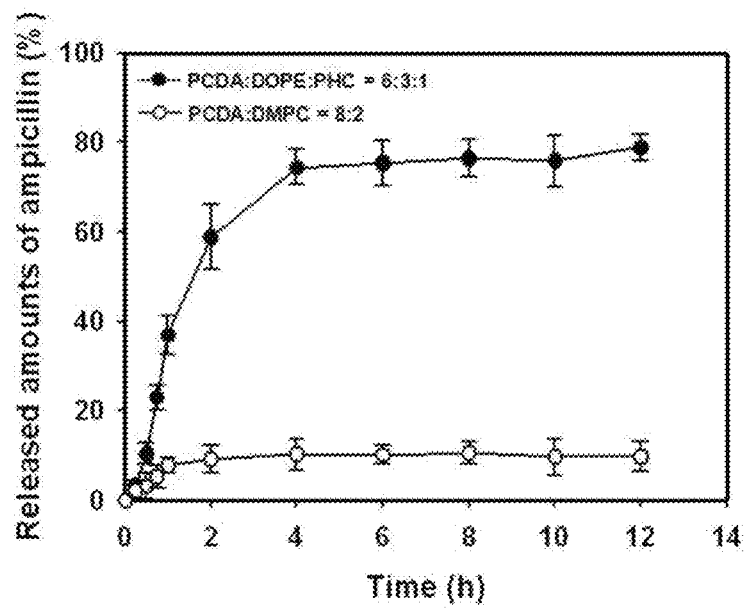
FIG. 4 is a graph showing a release amount of ampicillin in a test tube from PDA liposomes having loaded ampicillin of Synthetic Example 2 and Comparative Example 2.

A release profile of the ampicillin in vitro is shown in FIG. 4 below. At the time of the drug release, an effect of the pH condition on the PDA liposome was researched in the study. As shown in FIG. 4 below, each amount (%) of the ampicillin released from the PCDA/DMPC liposome and the PCDA/DOPE/PHC liposome within 2 hours was 9.21±3.14% and 57.42±7.35%. In the release profile, under an acidic pH condition (pH 4), the ampicillin in the pH sensitive PCDA/DOPE/PHC liposome according to the present invention was rapidly released and completely released within approximately 4 hours. On the contrary, the existing PCDA/DMPC liposome released a small amount of ampicillin due to liposome aggregation and drug diffusion as time passed. After 12 hours passed, each amount of the released ampicillin in two groups was 9.75±3.31% and 78.84±2.83%. 75% or more of the encapsulated ampicillin was released in the novel liposome according to the present invention. Meanwhile, after 12 hours, only 10% of the encapsulated ampicillin was released from the existing liposome. Therefore, the existing liposome was not affected by a low pH condition. The drug release rate was slightly decreased as time required for constant temperature culture was increased. However, a sustained drug release pattern in which the drug is slowly released was observed in both cases.

Therefore, the ampicillin release from the PCDA/DOPE/PHC liposome according to the present invention is rapid as compared to the release from the PCDA/DMPC liposome under the same pH, which indicates that the drug may be rapidly and successfully released from the novel pH sensitive liposome under an acidic pH condition.

(2) Confirmation of Drug Release In Vitro by Antibacterial Analysis

Figure 5:
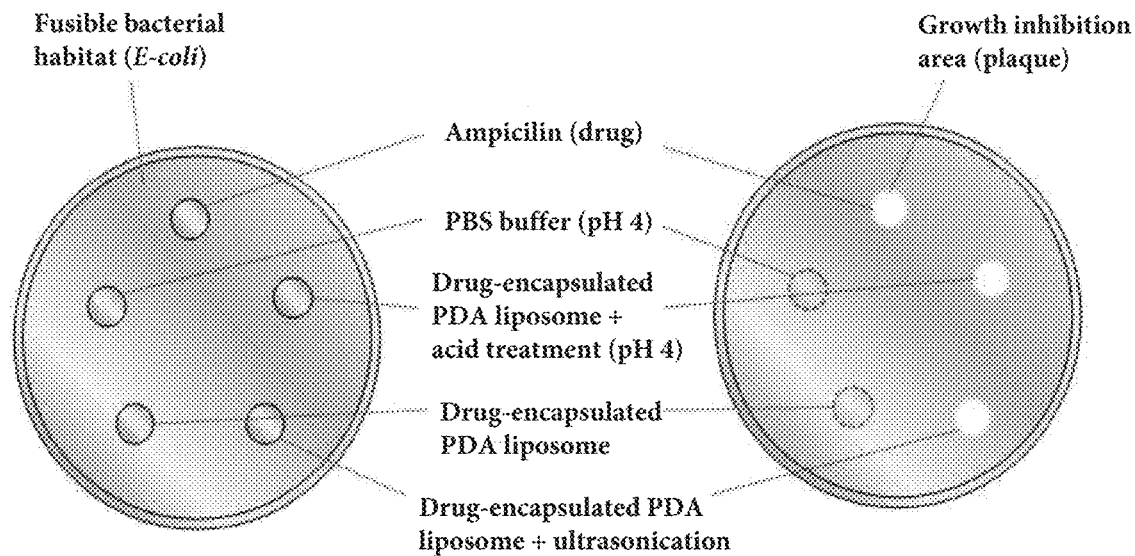
FIG. 5 is a conceptual diagram showing an anti-bacterial analysis for confirmation of drug release according to an embodiment of the present invention.

In order to confirm the drug release of the novel liposome according to the present invention in an appropriate vitro system, simple and reliable anti-bacterial analysis was used as shown in FIG. 5 below.

First, a growth inhibition area (plaque) will be shown in the fusible bacterial habitat in the case in which the drug is smoothly released from the liposome. In addition, the following specific requirements need to be satisfied in the analysis of the ampicillin encapsulated liposome. First, the encapsulated drug needs to maintain biological activity thereof. Second, all drugs in the liposome need to be available for the analysis, which requires complete release. Third, the analysis method needs to be quantitative.

Typical results of the anti-bacterial analysis on the ampicillin encapsulated pH sensitive PDA liposome were shown in FIG. 6 below.

Dishes (a), (b), and (d) are control groups, wherein the dish (a) is a non-treated dish, the dish (b) is a plate cultured dish using PBS buffer (pH 4), the dish (d) is a plate cultured dish using a drug-encapsulated liposome suspended in the PBS buffer.

Figure 6:
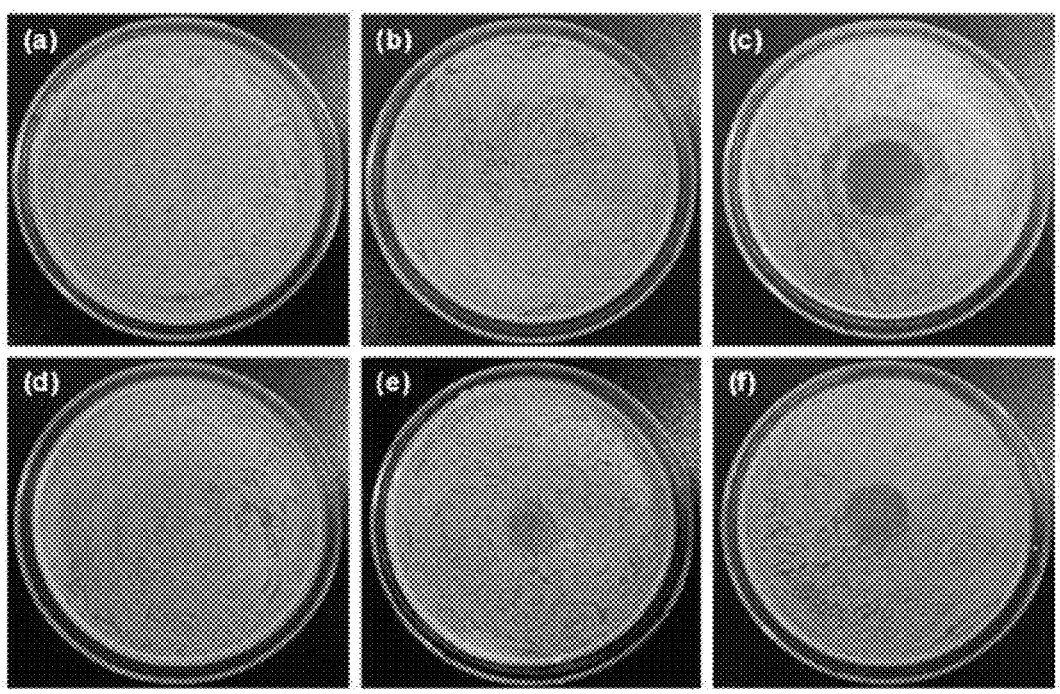
FIG. 6 is an image showing typical results of anti-bacterial analysis using the pH sensitive PDA liposome drug delivery vehicle in which ampicillin is encapsulated and loaded according to the present invention, wherein (a) shows a non-treated liposome, (b) shows PBS buffer (pH 4), (c) shows ampicillin standard solution (solution of PBS), (d) shows an ampicillin-encapsulated liposome, (e) shows an acid-treated ampicillin-encapsulated liposome (pH 4), and (f) shows an ultrasonic-treated ampicillin-encapsulated liposome.

As shown in FIG. 6 below, the growth inhibition area was not shown in these control groups. In particular, the absence of the growth inhibition area in the dish (d) proves that the novel liposome system according to the present invention is significantly stable and may prevent an undesirable release of ampicillin causing side effects.

On the contrary, when the ampicillin agent is used, the growth inhibition area was generally observed. The dish (c) showed a typical reaction with the ampicillin standard solution. The dishes (e) and (f) showed reactions of the acid-treated drug encapsulated liposome and the ultrasonic-treated drug encapsulated liposome under a pH 4 condition, respectively. For a complete drug release, a vesicle structure of the drug encapsulated liposome was destroyed by a probe ultrasonic processor with the maximum power. The ampicillin released from the pH sensitive PDA liposome according to the present invention biologically functioned to kill the bacteria, which was confirmed by the presence of the growth inhibition area in the bacterial habitat. In addition, the amount of the released drug could be analyzed by measuring a diameter of the growth inhibition area.

(3) Fluorescent Analysis for Monitoring of Drug Release

Since fluorescent release is shown by a structural change according to various external stimulations such as pH condition, and the like, the drug delivery of the pH sensitive PDA liposome according to the present invention may be monitored under various pH conditions by a fluorescent-generation method. Therefore, fluorescent images of the pH sensitive PDA liposome were obtained and intensity was measured.

Figure 7:
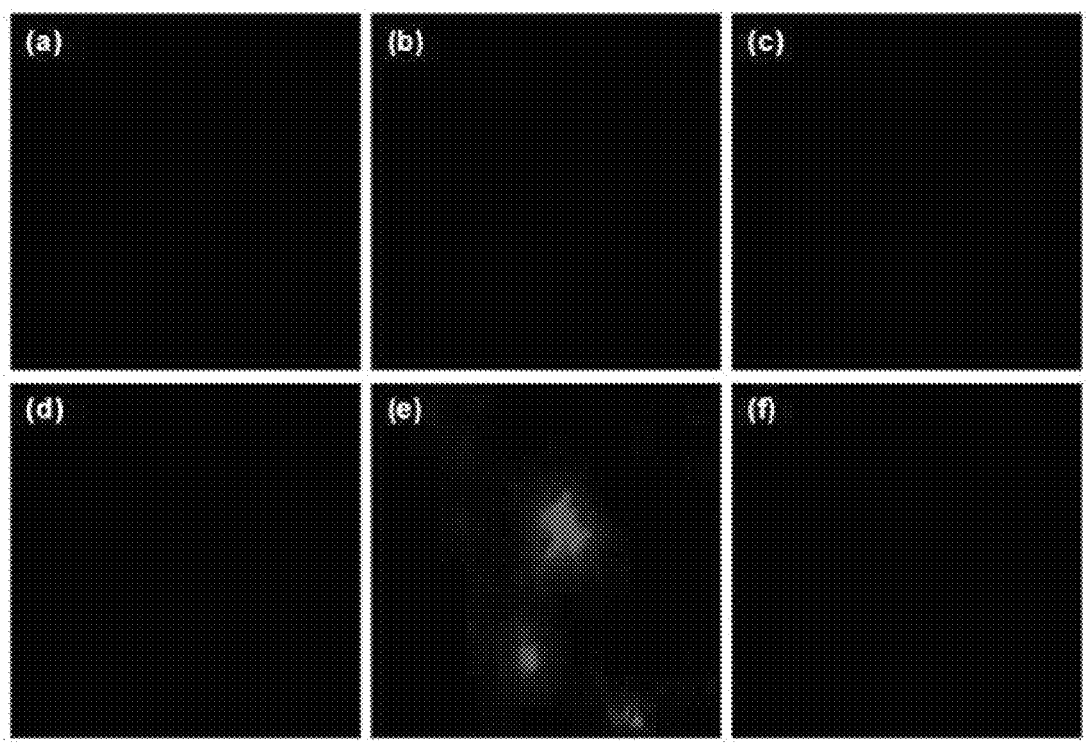
FIG. 7 shows fluorescent images of a growth inhibition area on a bacterial medium in each plate, wherein (a) shows a non-treated liposome, (b) shows PBS buffer (pH 4), (c) shows an ampicillin standard solution (solution of PBS), (d) shows an ampicillin-encapsulated liposome, (e) shows an acid-treated ampicillin-encapsulated liposome (pH 4), and (f) shows an ultrasonic-treated ampicillin-encapsulated liposome.

FIG. 7 below shows fluorescent images of the growth inhibition area on the bacterial medium in each plate, wherein only the dish (e) showed a clear fluorescent image of the growth inhibition area due to the PDA liposome-liposome fusion induced by an acid and a change in shape. However, the dish (f) in which the ultrasonic-treated PDA liposome solution was dropped does not have the fluorescent image. In the dish (f), fluorescence was lost due to the liposome structure in which the PDA liposome is completely conflicted.

In addition, the existing polymer liposomes consisting of PCDA and DMPC (Comparative Examples 1 and 2) were compared with the novel pH sensitive liposomes (Synthetic Examples 1 and 2) consisting of PCDA, DOPE and PHC according to the present invention under an acidic condition.

Figure 8:
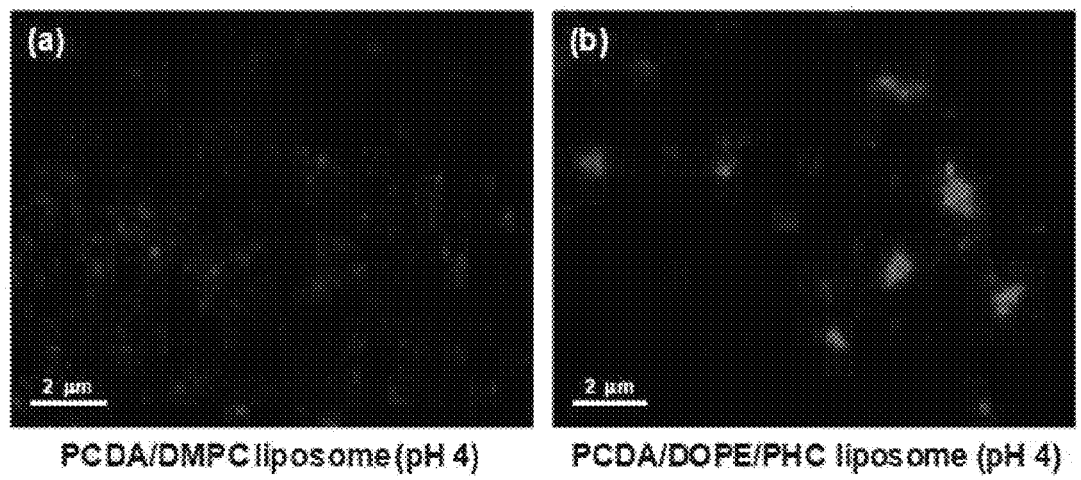
FIG. 8 shows fluorescent images of (a) Comparative Example 2 and (b) Synthetic Example 2 under an acidic pH condition (pH 4).
Figure 9:
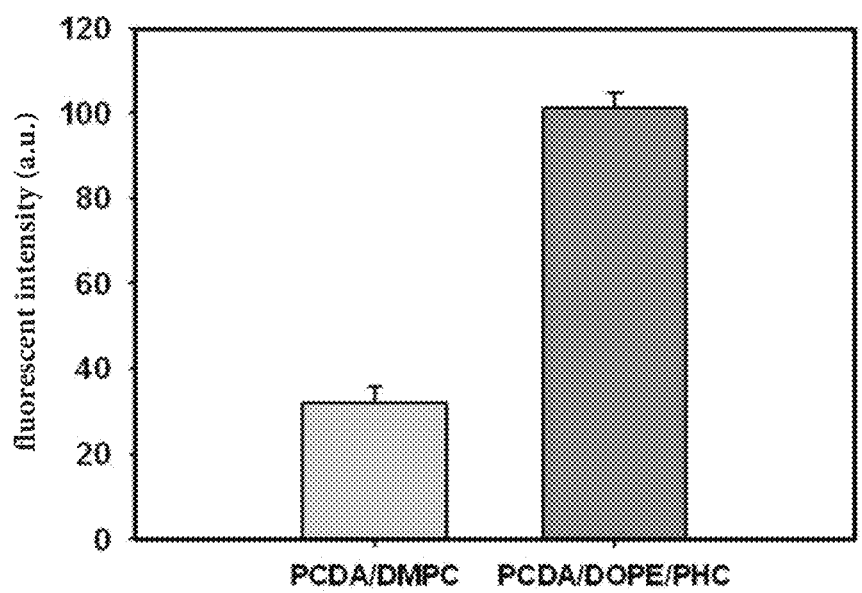
FIG. 9 shows fluorescent intensity of (a) Comparative Example 2 and (b) Synthetic Example 2 under an acidic pH condition (pH 4).

As shown in FIGS. 8 and 9, the existing PDA liposome showed a single red spot fluorescent image, and fluorescent intensity was slightly increased under the acidic condition (pH 4). Meanwhile, the novel pH sensitive PDA liposome was generally aggregated and showed a strong red spot fluorescent image due to the liposome-liposome fusion. In addition, after the acid treatment, the fluorescent intensity was remarkably increased, which is induced by significant change in the structure of the PDA liposome. The pH sensitive PDA liposome may be easily differentiated from other liposomes under the acidic pH condition.

Therefore, when the novel pH sensitive PDA liposome according to the present invention is utilized as the drug delivery vehicle, the drug may be controlled to be automatically released under a specific pH condition, and the drug may be selectively released under the specific pH condition. In addition, by measuring the fluorescent images and intensity of the novel pH sensitive PDA liposome according to the present invention, real-time monitoring of the drug release may be performed in vitro and in vivo under an acidic pH condition, which is similar to the case of a tumor cell.

INDUSTRIAL APPLICABILITY

As described above, the novel PDA liposome according to the present invention may be effectively utilized as a nano carrier for drug delivery. In particular, with the PDA liposome drug delivery vehicle according to the present invention, sensitivity may be improved under an acidic condition by mixing various types of lipids with each other. As a result obtained by measuring shapes of the liposome and particle size distribution in various pHs, it may be confirmed that a shape and a size of the liposome consisting of PCDA, DOPE and PHC may be easily changed by liposome-liposome fusion. In addition, the drug release in acidic pH may be easily controlled, and the drug release efficiency may be confirmed by observing fluorescent images and measuring fluorescent intensity.

What is claimed is:

1. A polydiacetylene liposome having an inner space isolated from a medium by a lipid layer membrane, wherein the lipid layer comprises 10,12-pentacosadiynoic acid (PCDA), 1,2-dioleoyl-sn-glycero-3-phosphoethanolamine (DOPE) and N-palmitoyl homocysteine (PHC), wherein a molar ratio of the PCDA, DOPE and PHC is 6:3:1.

2. The polydiacetylene liposome of claim 1, wherein the polydiacetylene liposome increases in diameter with decreasing pH.

3. The polydiacetylene liposome of claim 1, wherein the polydiacetylene liposome fluoresces inherently in response to an environmental stimulus comprising a change in pH, to produce a real-time monitorable fluorescence.

4. A drug delivery vehicle comprising a polydiacetylene liposome having an inner space isolated from a medium by a lipid layer membrane, wherein the lipid layer comprises 10,12-pentacosadiynoic acid (PCDA), 1,2-dioleoyl-sn-glycero-3-phosphoethanolamine (DOPE) and N-palmitoyl homocysteine (PHC), and the drug to be delivered is encapsulated in the isolated inner space of the polydiacetylene liposome, wherein a molar ratio of the PCDA, DOPE and PHC is 6:3:1.

5. The drug delivery vehicle of claim 4, wherein the liposome increases in diameter with decreasing pH.

6. The drug delivery vehicle of claim 5, wherein the drug in the liposome is released when the polydiacetylene liposome is fused with the adjacent polydiacetylene liposome, and during the drug release, the polydiacetylene liposome itself fluoresces inherently by environmental stimulus, and the fluorescence can be monitored in real-time.

7. The drug delivery vehicle of claim 4, wherein the drug is an anti-biotic drug or an anti-cancer drug.

8. A drug delivery method using the drug delivery vehicle of claim 4, wherein the drug delivery vehicle controls a drug release time and a drug release amount by the following steps:

(a) controlling the drug release time by controlling pH of the medium within a range of pH 3 to pH 7 with respect to the drug delivery vehicle;

(b) expressing inherent fluorescence of the liposome according to a pH change which is an external stimulus while releasing the drug by controlling the drug release time at same time; and (c) confirming and monitoring the drug release and the drug release amount in real-time by measuring the fluorescence intensity of the liposome.

\* \* \* \* \*